(12) United States Patent
Calluaud et al.

(10) Patent No.: US 8,397,716 B2
(45) Date of Patent: *Mar. 19, 2013

(54) METHOD AND APPARATUS FOR SUBSTANCE DELIVERY IN SYSTEM FOR SUPPLYING BREATHABLE GAS

(75) Inventors: Michel Calluaud, Bayview (AU); Victor Yerbury, Wahroonga (AU)

(73) Assignee: ResMed Limited, Bella Vista (AU)

( * ) Notice: Subject to any disclaimer, the term of this patent is extended or adjusted under 35 U.S.C. 154(b) by 32 days.

This patent is subject to a terminal disclaimer.

(21) Appl. No.: 12/837,784

(22) Filed: Jul. 16, 2010

(65) Prior Publication Data

US 2010/0282251 A1    Nov. 11, 2010

Related U.S. Application Data

(63) Continuation of application No. 11/237,830, filed on Sep. 29, 2005, now Pat. No. 7,779,834, which is a continuation of application No. 09/466,971, filed on Dec. 20, 1999, now Pat. No. 6,990,977, which is a continuation of application No. 08/989,150, filed on Dec. 12, 1997, now Pat. No. 6,029,660.

(30) Foreign Application Priority Data

Dec. 12, 1996    (AU) ...................................... PO4186

(51) Int. Cl.
*A61M 16/00*    (2006.01)
*A61M 16/01*    (2006.01)
*A61M 16/10*    (2006.01)

(52) U.S. Cl. ......... 128/203.12; 128/204.21; 128/203.29; 128/204.18; 128/204.26

(58) Field of Classification Search ............. 128/203.12, 128/203.15, 203.16, 203.19, 200.24, 203.22, 128/203.25, 203.29, 204.18, 204.21, 204.22, 128/204.26, 205.11, 205.25, 200.21, 204.23

See application file for complete search history.

(56) References Cited

U.S. PATENT DOCUMENTS

| | | |
|---|---|---|
| 2,208,633 A | 7/1940 | Heidbrink |
| 3,662,751 A | 5/1972 | Barkalow et al. |
| 4,127,121 A | 11/1978 | Westenskow et al. |
| 4,141,355 A | 2/1979 | Apple |
| 4,155,356 A | 5/1979 | Venegas |
| 4,207,887 A | 6/1980 | Hiltebrandt et al. |
| 4,210,136 A | 7/1980 | Apple |
| 4,265,237 A | 5/1981 | Schwanbom et al. |
| 4,307,730 A | 12/1981 | Korn |
| 4,375,346 A | 3/1983 | Kraus et al. |
| 4,538,604 A | 9/1985 | Usry et al. |
| 4,558,710 A | 12/1985 | Eichler |
| 4,565,194 A | 1/1986 | Weerda et al. |
| 4,770,168 A | 9/1988 | Rusz et al. |
| 4,819,629 A | 4/1989 | Jonson |
| 4,832,014 A | 5/1989 | Perkins |
| 4,932,401 A | 6/1990 | Perkins |
| 4,986,269 A | 1/1991 | Hakkinen |
| 5,107,830 A | 4/1992 | Younes |
| 5,239,994 A | 8/1993 | Atkins |

(Continued)

FOREIGN PATENT DOCUMENTS

| | | |
|---|---|---|
| DE | 3015279 | 10/1981 |
| DE | 3537507 | 4/1987 |

(Continued)

*Primary Examiner* — Clinton T Ostrup
(74) *Attorney, Agent, or Firm* — Nixon & Vanderhye P.C.

(57) ABSTRACT

A substance delivery apparatus for use with a system for supplying breathable gas to a human or animal includes a sensor to measure the pressure of the supplied breathable gas and to detect inhalation by the human or animal; and a reservoir, a conduit, a pump, and a diaphragm to deliver the substance to the human or animal during inhalation at a pressure higher than the supplied pressure of the breathable gas.

34 Claims, 7 Drawing Sheets

U.S. PATENT DOCUMENTS

| | | | |
|---|---|---|---|
| 5,277,175 A | 1/1994 | Riggs et al. | |
| 5,404,871 A | 4/1995 | Goodman | |
| 5,423,313 A | 6/1995 | Olsson et al. | |
| 5,479,220 A | 12/1995 | Komatsu et al. | |
| 5,479,920 A | 1/1996 | Piper | |
| 5,497,944 A | 3/1996 | Weston et al. | |
| 5,503,146 A | 4/1996 | Froehlich et al. | |
| 5,540,220 A | 7/1996 | Gropper et al. | |
| 5,546,931 A * | 8/1996 | Rusz | 128/203.12 |
| 5,560,353 A | 10/1996 | Willemot et al. | |
| 5,570,682 A | 11/1996 | Johnson | |
| 5,572,993 A | 11/1996 | Kurome et al. | |
| 5,608,647 A | 3/1997 | Rubsamen | |
| 5,642,730 A | 7/1997 | Baran | |
| 5,649,531 A | 7/1997 | Heinonen | |
| 5,651,358 A | 7/1997 | Briend et al. | |
| 5,655,520 A | 8/1997 | Howe | |
| 5,666,946 A | 9/1997 | Langenback | |
| 5,839,433 A | 11/1998 | Higenbottam | |
| 5,845,633 A | 12/1998 | Psaros | |
| 5,865,173 A | 2/1999 | Froehlich | |
| 5,967,141 A | 10/1999 | Heinonen | |
| 5,971,723 A * | 10/1999 | Bolt et al. | 417/413.1 |
| 6,006,748 A | 12/1999 | Hollis | |
| 6,029,660 A | 2/2000 | Calluaud et al. | |
| 6,990,977 B1 | 1/2006 | Calluaud et al. | |

FOREIGN PATENT DOCUMENTS

| | | |
|---|---|---|
| DE | 19525557 A1 | 10/1999 |
| EP | 0178925 | 4/1986 |
| GB | 2164569 | 3/1986 |
| WO | 86/06969 | 12/1986 |
| WO | 92/15353 | 9/1992 |
| WO | 94/16759 | 8/1994 |
| WO | 97/03290 | 1/1997 |

* cited by examiner

METHOD AND APPARATUS FOR SUBSTANCE DELIVERY IN SYSTEM FOR SUPPLYING BREATHABLE GAS

CROSS-REFERENCES TO RELATED APPLICATIONS

This is a continuation of application Ser. No. 11/237,830, filed Sep. 29, 2005, now allowed, which is a continuation of application Ser. No. 09/466,971, filed Dec. 20, 1999, now U.S. Pat. No. 6,990,977, which is a continuation of application Ser. No. 08/989,150, filed Dec. 12, 1997, now U.S. Pat. No. 6,029,660, which claims priority to Australian Application No. PO4186, filed Dec. 12, 1996, each incorporated herein by reference in its entirety.

FIELD OF THE INVENTION

The present invention relates to a substance delivery apparatus for use with a system for supplying breathable gas to a human or animal.

BACKGROUND OF THE INVENTION

Treatment of Obstructive Sleep Apnea (CSA) with Continuous Positive Airway Pressure (CPAP) flow generator systems involves the continuous delivery of a breathable gas (generally air) pressurised above atmospheric pressure to a patient's airways via a conduit and a mask. CPAP pressures of 4 cm $H_2O$ to 22 cm $H_2O$ are typically used for treatment of OSA, depending on patient requirements. Treatment pressures for assisted ventilation can range of up to 32 cm $H_2O$ and beyond, again depending on patient requirements.

For either the treatment of OSA or the application of assisted ventilation or similar, the pressure of the gas delivered to patients can be constant level, bi-level (in synchronism with patient inspiration) or auto setting in level. Throughout the specification reference to CPAP is intended to incorporate a reference to any one of, or combinations of, these forms of pressurised gas supply.

It is difficult to administer substances such as medicines to patients undergoing CPAP treatment without interrupting the treatment by removing the gas supply mask.

It is an object of the present invention to ameliorate the above disadvantage.

SUMMARY OF THE INVENTION

In a first aspect, the present invention provides a substance delivery apparatus for use with a system for supplying breathable gas to a human or animal, the apparatus including:
  means to measure the pressure of the supplied breathable gas;
  means to detect inhalation by the human or animal; and
  means to deliver the substance to the human or animal during inhalation at a pressure higher than the supplied pressure of the breathable gas.

In a second aspect the invention provides a method of delivering a substance to a human or animal being supplied with breathable gas, the method includes the steps of:
  measuring the pressure of the supplied breathable gas;
  detecting inhalation by the human or animal; and
  delivering the substance to the human or animal during inhalation at a pressure higher than the supplied pressure of the breathable gas.

The substance is preferably a medicinal substance and, desirably, in the form of a gas, mist, aerated suspension, jet, spray, gas mixture or the like.

The substance is preferably delivered to the respiratory system of the human or animal and, in particular, to the nasal airways.

The supplied breathable gas is preferably pressurised above atmospheric pressure. The system for supplying the breathable gas preferably includes a pressurized gas flow generator in fluid communication with a mask worn by the human or animal is via a flexible conduit, and the inhalation detection means includes an airflow sensor adapted to measure the volumetric flow rate of the breathable gas passing through the conduit and generate a first input signal indicative of the breathable gas flow rate. The term mask is herein understood to include facemasks, nosemasks, mouthmask, apenditures in the vicinity of any of these masks and the like.

The first signal is preferably amplified by a first amplifier into a second input signal also indicative of the gas flow rate. A derivative of the first signal is also generated by a differentiating filter to determine the acceleration or deceleration of the gas, which is indicative of inhalation or exhalation respectively, and is represented by a third input signal.

When the airflow sensor is disposed downstream of the mask's vent to atmosphere then inhalation can be detected by sensing a reversal of the direction of the gas flow through the vent. Inhalation can also be detected by sensing an interruption of the gas flow.

The apparatus preferably also includes means to measure the volume of the substance to be delivered to the human or animal.

The pressure measuring means is preferably a pressure transducer connected to the conduit which is adapted to generate a fourth input signal indicative of the pressure of the gas in the conduit. The fourth input signal is preferably amplified by a second amplifier into a fifth input signal also indicative of the as pressure.

The substance delivery means is preferably a positive displacement pump, most preferably a diaphragm pump. The diaphragm pump is desirably in fluid communication with a substance reservoir via a one-way valve adapted to allow the substance to only pass from the reservoir to the pump. The pump is preferably also in fluid communication with the gas supply conduit via a one-way valve adapted to allow the substance to only pass from the pump to the conduit.

The diaphragm of the pump is desirably displaced by a linear drive means which, in one form, may take the form of an electromagnet. In other forms, a rotary drive means such as an electric DC motor, an electric AC motor, a stepper motor, or a brushless motor are used with a rotary to linear converter interposed between the rotary drive means and the diaphragm pump.

The apparatus preferably also includes a first control system adapted to receive the second, third and fourth input signals. The control system preferably also includes input means adapted to allow the input of a predetermined sixth input indicative of the volume of the substance to be delivered and a predetermined seventh input signal indicative of the amount by which the pressure of the delivered substance should exceed the pressure of the supplied breathable gas. The first control system is preferably adapted to receive the second, third, fifth, sixth and seventh input signals to calculate and generate a first output signal indicative of the amount of displacement of the linear or rotary drive means and a second output signal indicative of the direction of the displacement required to produce negative or positive pumping pressure.

The first and second output signals are preferably sent to a second control system which converts them into third and fourth output signals indicative of drive means displacement and direction respectively, the third and fourth output signals being compatible with the linear or rotary drive means.

Preferably, the first and second output signals are sent to a second control system adapted to convert them into third and fourth output signals indicative of drive means displacement and direction respectively, the third and fourth output signals being compatible with the linear or rotary drive means.

The input and output signals can be analog, digital or the like.

The described embodiments have been developed primarily for use in delivering medicinal substances co patients using Continuous Positive Airway Pressure (CPAP) gas delivery systems in, for example, the treatment of Obstructive Sleep Apnea (OSA) or similar sleep disorder breathing conditions.

The invention will be described hereinafter with reference to these applications. However, it will be appreciated that the invention is nor limited to this particular field of use. As examples, the invention may also be used in conjunction with suitable mask and gas delivery systems for other treatments such as assisted ventilation, assisted respiration or mechanical ventilation.

BRIEF DESCRIPTION OF THE DRAWINGS

Preferred embodiments of the invention will now be described, by way of example only, with reference to the accompanying figures in which.

DETAILED DESCRIPTION OF THE INVENTION

Figure 1:
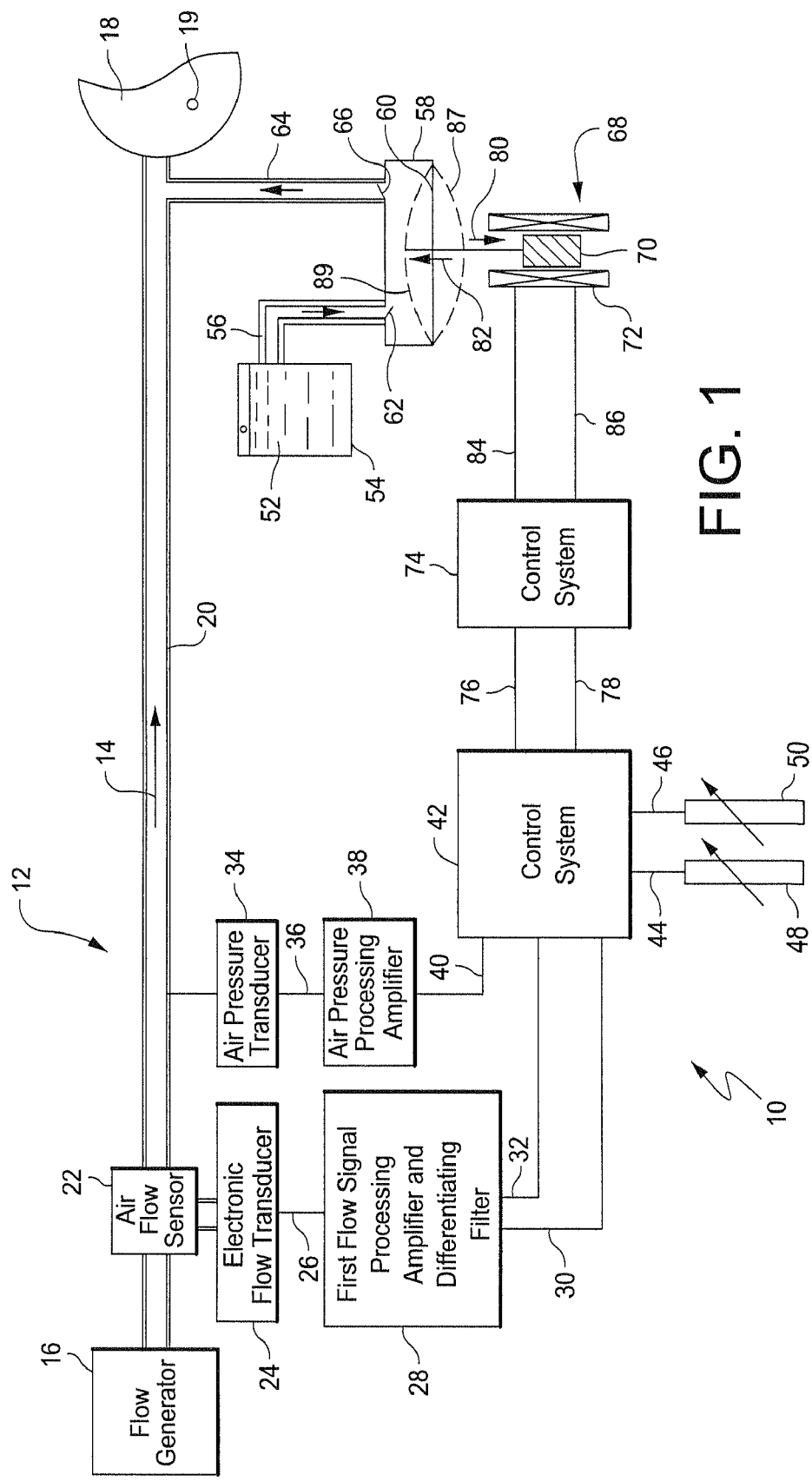
FIG. 1 is a schematic diagram of a substance delivery apparatus according to a first embodiment of the invention.

Referring firstly to FIG. 1, there is shown a first embodiment of a substance delivery apparatus 10 according to the invention. The apparatus 10 is used with a system, indicated generally at 12, for supplying air, indicated by arrow 14, to a human patient (not shown). The system 12 includes a pressurised gas flow generator 16 in fluid communication with a mask 18 via conduit 20. Mask 18 includes a gas washout vent 19.

The apparatus 10 includes a means to measure the pressure of the air 14 and to detect patient inhalation, in the form of an air flow sensor 22. The sensor 22 is interposed in the conduit 20 between the mask 18 and the pressurised gas flow generator 16. The airflow sensor 22, in the form of a fixed orifice, is connected to an electronic flow transducer 24. A variable orifice, venturi tube, Pitot tube or tubes bundle can also be used to sense airflow. The transducer 24 generates a first electrical input signal 26 indicative of the flow rate of the air 14 passing through the conduit 20 which is sent to a first flow signal processing amplifier and differentiating filter 28 which in turn generates second and third input signals 30 and 32 respectively.

The second input signal 30 is an amplified version of the first input signal 26. The third input signal 32 is the derivative of the first signal 26, with acceleration and deceleration being respectively indicative of inhalation or exhalation. When a patient inhales they apply suction to the air being delivered thus causing acceleration. Upon exhalation the air being delivered is obstructed by the exhaled air flowing in the opposite direction thus causing deceleration.

An air pressure transducer 34 is also connected to the conduit 20 and generates a fourth electrical input signal 36 indicative of the pressure in the conduit. The fourth signal 36 is delivered to an air pressure processing amplifier 38 which generates a fifth input signal 40 also indicative of the pressure in the conduit 20.

The second, third and fifth input signals 30, 32 and 40 are fed to a first control system 42. The first control system 42 also receives sixth and seventh predetermined input signals 44 and 46 from manual inputs 48 and 50 in the form of potentiometers accessible by a system operator. Variable resistors can also be used as the manual inputs. The sixth input signal 44 is indicative of the volume of substance to be delivered to the mask during each inhalation cycle of the patient. The seventh signal 46 is indicative of the amount by which the delivery pressure of the substance is to exceed the measured pressure of the air 14 in the conduit 20.

The means to deliver a substance 52 to the mask 18 includes a substance reservoir 54 connected by conduit 56 to diaphragm pump 58 having a flexible diaphragm 60. A one way valve 62 is interposed between the reservoir 54 and pump 58 and permits the substance 52 to only enter the pump 58. The pump 58 is in fluid communication with the conduit 20 by virtue of conduit branch 64 and one way valve 66 which allows the substance 52 to pass from the pump 58 to the conduit 20.

The stroke of the diaphragm 60 is controlled by an electromagnet drive means 68, in the form of a magnet 70 connected to the centre of the diaphragm 60 and surrounded by electrical windings 72. The drive means 68 are controlled by a second control system 74.

In response to receiving the second, third, fifth, sixth and seventh input signals, the first control system 42 generates first and second output signals 76 and 78, respectively indicative of the electromagnet displacement magnitude and direction. Displacement in the direction of arrow 80 draws the substance 52 into the pump 58. Displacement in the direction of arrow 82 causes the substance 52 to be pumped into the conduit branch 64 and thereafter the conduit 20. The output signals 76 and 78 are received by the second control system 74 which issues third and fourth output signals 84 and 86 respectively, which are compatible with the drive means 68. The third output signal 84 is indicative of the amount of displacement of the electromagnet 68 and the fourth signal 86 is indicative of the displacement direction.

In use, when the system is switched on, breathable air 14 is supplied by the gas flow generator 16 to the mask 18 via the conduit 20) so the patient may breathe.

As the patient inhales, an analogue to digital converter (not shown) in the control system 42 samples the air flow information of the second input signal 30 over a few breaths and stores it in a memory (not shown). The stored values are integrated with respect, to the time of the inhalation portion of their respective breathing cycle. The integrated value is the tidal volume of each breath and is also stored in the memory. The stored values of the tidal volume are averaged over a small number of breaths to provide an average value of the tidal volume.

From the average value of the tidal volume and the setting of the manual input 48 the volume of the substance 52 (ie, the drug or gas) to be delivered for each breath is calculated. The control system 42 also calculates the magnitude of the current to be applied to the windings 72 of the diaphragm pump 58.

When the third input signal 32 indicates exhalation, the control systems 42 and is 74 calculate and issue the third and fourth output signals 84 and 86 to the windings 72. The direction of the current applied to the windings 72 causes the magnet 70 and the diaphragm 60 to be displaced in the direction of the arrow 80 to the position shown by phantom line 87. This movement of the diaphragm 60 draws the substance 52 past the one way valve 63 and into the pump 58. The magnitude of the current applied to windings 72 is proportional to the displacement of the diaphragm 60 and also therefore the volume of gas drawn into the pump 58 which is delivered to the patient during the next inhalation cycle. At the end of the patient exhalation cycle the current applied to the windings 72 remains constant and the magnet 70 and diaphragm 60 remain as indicated by line 87.

When the third input signal 32 indicates inhalation, the control system 42 and 74 reverse the current flowing into the windings 72, thereby displacing the magnet 70 and the diaphragm 60 in the direction indicated by the arrow 82 to the position shown by phantom line 89. This movement forces the substance 52 from the pump 53 through the one way valve 68 and conduit branch 64 into the mask 18.

The air pressure of the gas 14 in the conduit 20 is exceeded by the pressure of the substance pumped through conduit branch 64. The supply pressure of the substance 52 is calculated by the control system 42 and is the sum of the pressure measured by pressure transducer 34 in conduit 20 and the pressure increment set by manual input 50. The substance 52 is then delivered to the patient via the conduit 64 and the mask 18.

Figure 2:
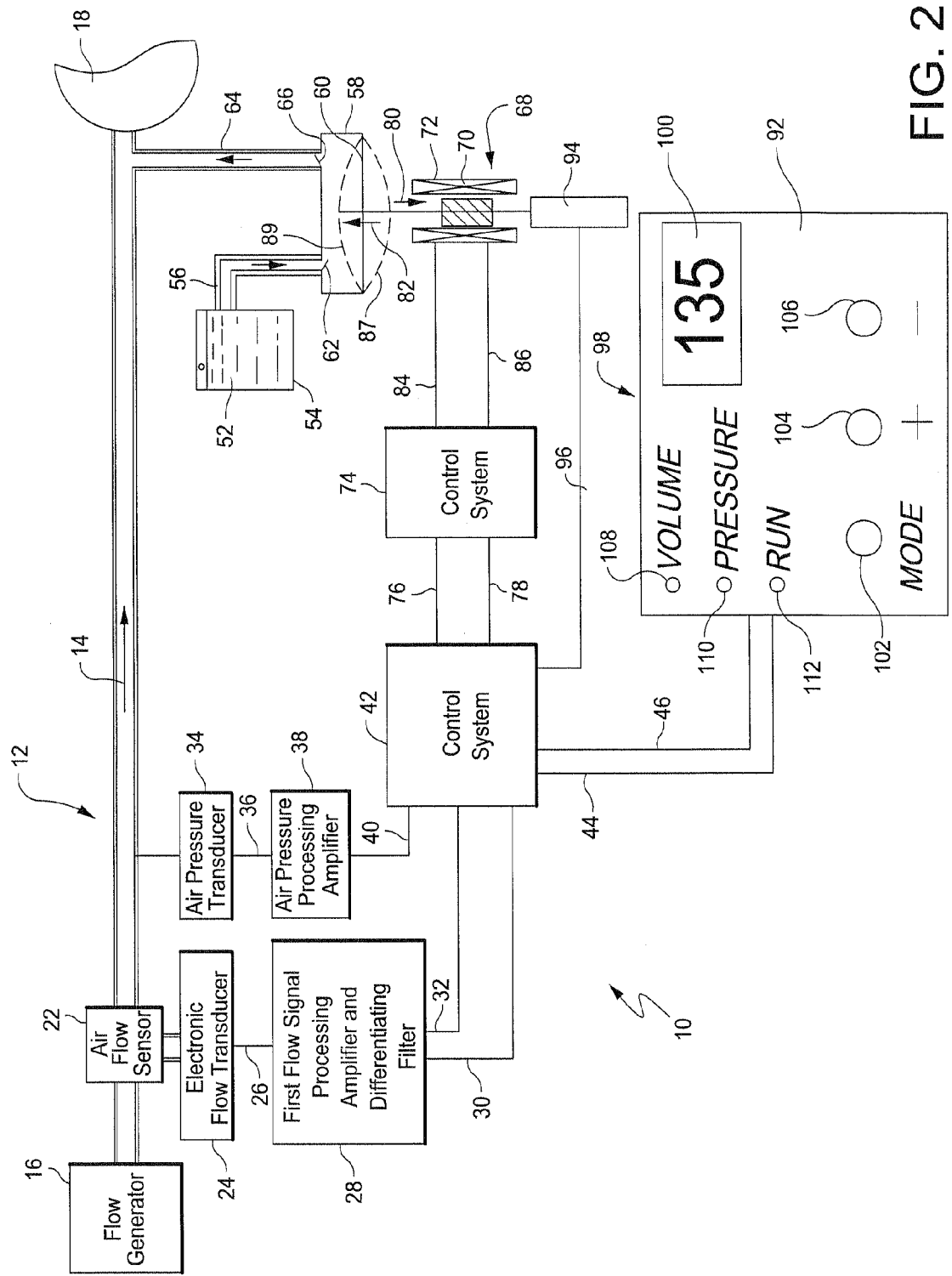
FIG. 2 is a schematic diagram of a substance delivery apparatus according to a second embodiment of the invention.

A second embodiment of the present invention is shown in FIG. 2, in which like reference numerals are used to indicate like features.

The first control system 42 of the second embodiment incorporates a microcontroller 92 and a linear position transducer 94 connected to the magnet 70 to provide a feedback signal 96 indicative of the position of the magnet 70 and the diaphragm 60, to which it is connected.

The two manual inputs 48 and 50 are replaced by a digital control panel 98 with: a three digit digital display 100; three push buttons: Mode 102, "+" 104, "−" 106; and three LEDs to indicate the mode selected: Volume 108, Delivery Pressure 110 and Run 112.

The operation of this system is generally similar to the description above except where indicated below.

Successive depression of the Mode push button 102 cycles through the three modes of operation: Volume, Delivery Pressure and Run.

When Volume or Delivery Pressure is selected, the digital display 100 indicates the current setting of that parameter. This value may be modified if required by operating either of the two push buttons "+" 104 or "−" 106.

Figure 3:
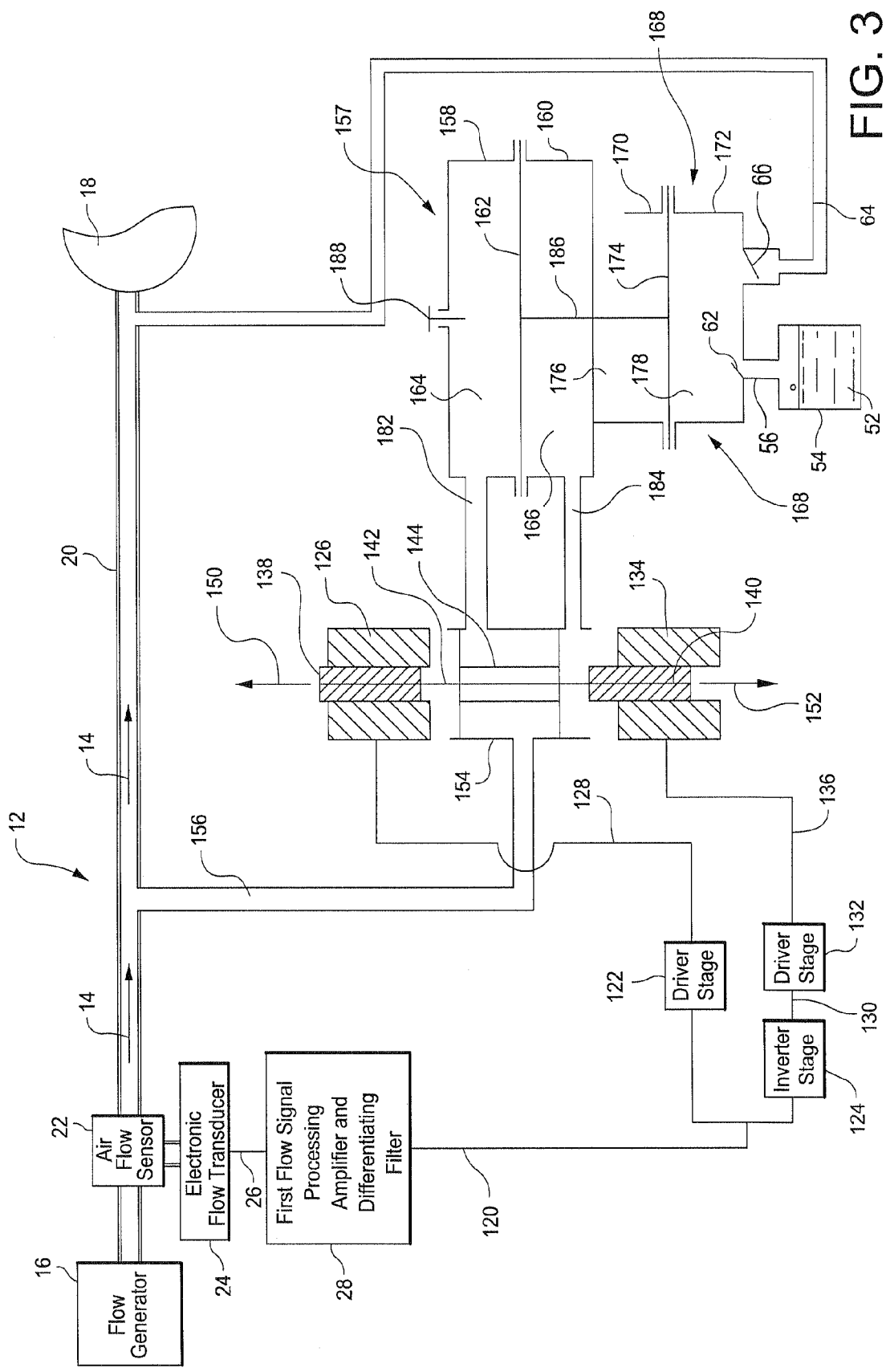
FIG. 3 is a schematic diagram of a substance delivery apparatus according to a third embodiment of the invention.
Figure 4:
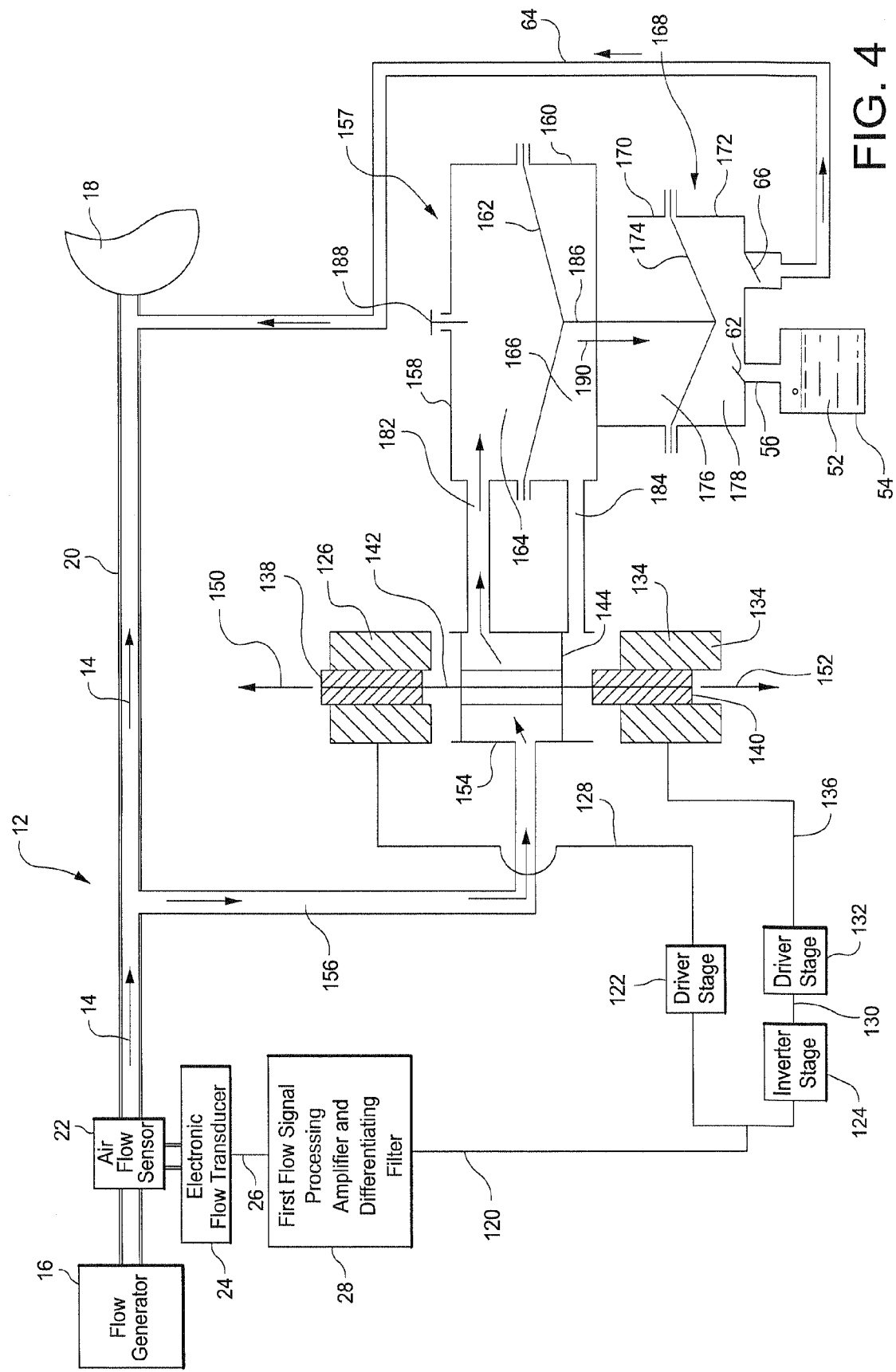
FIG. 4 is a schematic diagram of the apparatus of FIG. 3 during inhalation.
Figure 5:
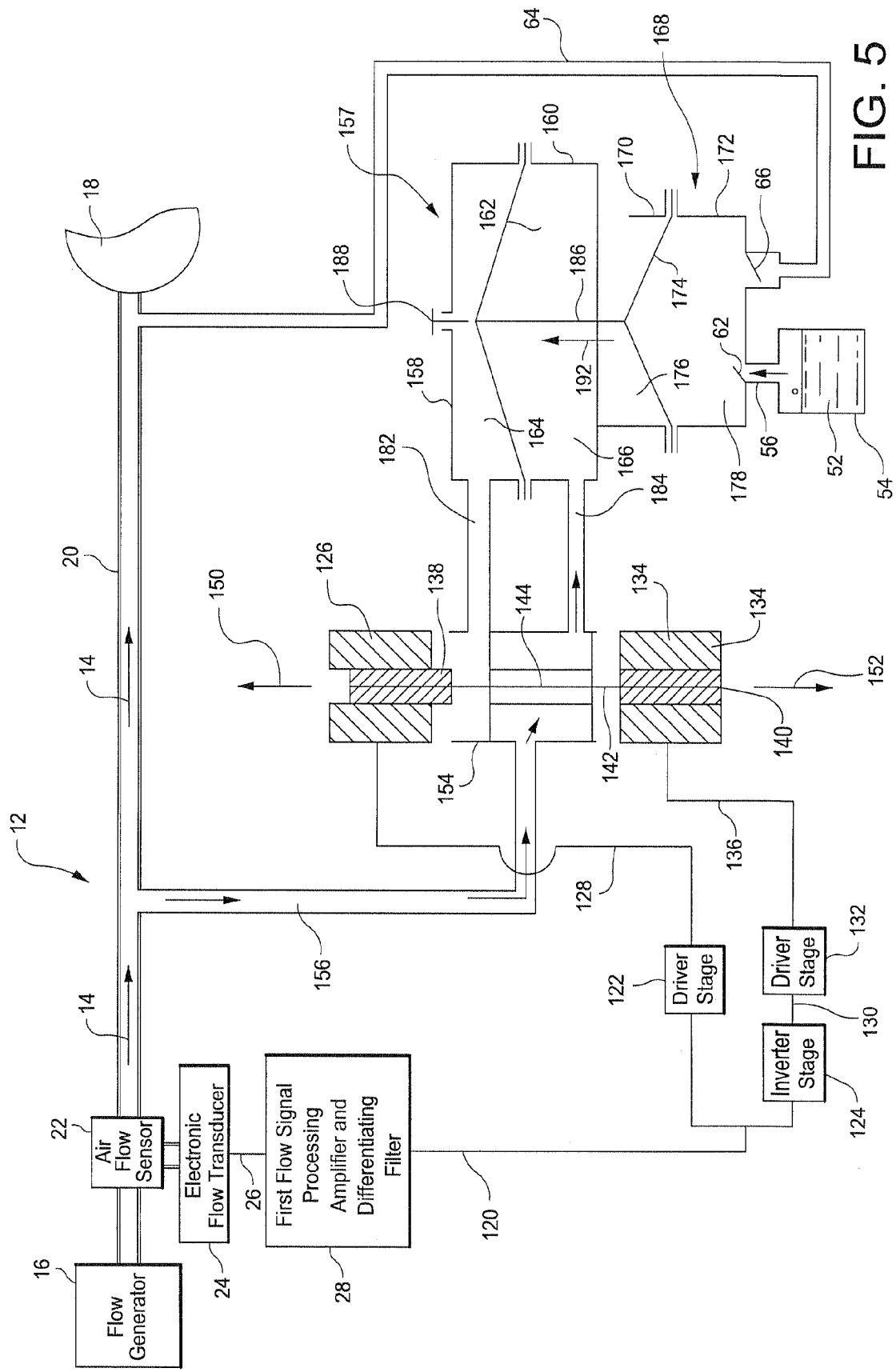
FIG. 5 is a schematic diagram of the apparatus shown in FIG. 3 during exhalation.

When Run is selected, the parameters stored in the memory of the microcontroller 90 calculate the desired position of the magnet 70. This is then compared with the actual magnet position indicated by the linear position transducer 94. Any difference produces an error signal that is used to correct the position of the magnet 70 to the desired position, A third embodiment of the present invention is shown in FIGS. 3 to 5, in which like reference numerals are again used to indicate like features. In this embodiment, the flow processing amplifier and differentiating filter 28 again detects the onset of inhalation by sensing a change in the rate of flow (i.e. the acceleration or deceleration) of the gas flowing past the sensor 22.

The output signal 120 from the amplifier filter 28 of this embodiment is active when the onset of inhalation is detected and remains active for the duration of the inhalation portion of the breathing cycle. The output signal 120 from the amplifier filter 28 is not active for the exhalation portion of the breathing cycle.

The output signal 120 is supplied to a driver stage 122 and an inverter stage 124.

When the output signal 120 is active, during inhalation, the driver stage 122 is active and applies power to an electromagnetic winding 126 through a connection 128. When the output signal 120 is inactive, during exhalation, the inverter stage 124 supplies a drive signal 130 to a driver stage 132. The driver sage 132 is activated and supplies power to an electromagnetic winding 134 through a connection 136.

A magnetic core 138 is located within the electromagnetic winding 126. Similarly, a magnetic core 140 is located within the electromagnetic winding 134.

The magnetic core 138 and the magnetic core 140 are connected by a connecting rod 142 which is also connected to a sliding spool valve 144.

When the winding 126 is energised through the connection 128 the magnetic core 138 is displaced in the direction of arrow 150 and pulls with it the spool valve 144 and core 140.

When winding 134 is energised through connection 136 the magnetic core 140 is displaced in the direction of arrow 152 and pulls with it the spool valve 144 and core 138.

The body 154 of the spool valve 144 is connected to the gas flow generator 16 through a branch conduit 156 connected to the conduit 20.

A diaphragm motor 157 is comprised of housing halves 158 and 160 separated by a diaphragm 162 which defines cavities 164 and 166. A diaphragm pump 168 is comprised of housing halves 170 and 172 separated by a diaphragm 174 which defines cavities 176 and 178. The cavity 164 is connected to the spool valve body 154 by a conduit 182. The cavity 166 is connected to the spool valve body 154 by a conduit 184. The cavity 176 is open to atmosphere. The cavity 178 is connected to the source 54 of the substance 52 to be delivered by the conduit 56 and the one-way valve 62. The cavity 178 is also connected to the mask 18 by the conduit 64 and the one-way valve 66.

The motor diaphragm 162 and the pump diaphragm 174 are connected by a connecting rod 186. The connecting rod 186 passes through an air sealed bearing (not shown) between cavities 166 and 176.

An adjusting screw 188 is located on the top of housing halve 158.

With reference to FIG. 4, the operation of the apparatus will be described during the inhalation portion of the breathing cycle.

As the patient start to inhale, the second output signal 120 from the flow processing amplifier 28 is set to active and activates the driver stage 122. The inverter stage 124 is inactive and magnetic core 140 is free to move. The driver stage 122 supplies power to the electromagnetic winding 126 through connection 128. The magnetic core 138 is forced in the direction of the arrow 150 and with it the spool valve 144. The air 14 now flows from the branch conduit 156 into the spool valve body 154 and is diverted by the spool valve 144 through the conduit 182 and into the cavity 164. The pressure of the air entering the cavity 164 forces the motor diaphragm 162 in the direction of arrow 190 and with it the pump diaphragm 174. The cavity 178 is already filled with the substance 52 to be delivered to the mask 18.

The displacement of the pump diaphragm 174 into the cavity 178 increases the substance pressure, closes the one-way valve 62, opens the one-way valve 66, and forces the substance 52 into the conduit 64. The conduit 64 is in fluid communication with the conduit 20 and the mask 18 and the substance 52 is thereby delivered to the mask 18 and the patient.

With reference to FIG. 5, the operation of the apparatus will be described during the exhalation portion of the breathing cycle.

As the patient start to exhale, the second output signal 120 from the flow processing amplifier 28 is set to inactive. The driver stage 122 is not activated and power is not supplied to the electromagnetic winding 126 through connection 128. The magnetic core 138 is therefore free to move. As the output signal 120 from the flow processing amplifier 28 is now inactive, the inverter stage 124 turns its output signal to active and activates the driver stage 132. The driver stage 132 supplies power to the electromagnetic winding 134 through the connection 136 and the magnetic core 140 is forced in the direction of the arrow 152 and with it the spool valve 144. The air flows from the branch conduit 156 into the spool valve body 154 and is diverted by the spool valve 144 through the conduit 184 into the cavity 166. The pressure of the air in the cavity 166 forces the motor diaphragm 162 in the direction of arrow 192 and with it the pump diaphragm 174. The displacement of pump diaphragm 174 into cavity 176 produces a vacuum in cavity 178, closes the one-way valve 66, opens the one-way valve 62, and draws the substance 52 through the conduit 56 into the cavity 178.

The movement of the motor diaphragm 162 and pump diaphragm 174 is limited by the adjusting screw 188. The setting of the screw 188 governs the maximum displacement of the motor diaphragm 162 and pump diaphragm 174 in direction of the arrow 192, therefore controlling the volume of the substance 52 able to be drawn into the cavity 178 for delivery to the patient during the next inhalation.

The pump diaphragm 174 is smaller in area than the motor diaphragm 162. Accordingly, a given pressure supplied to motor diaphragm 162 will produce a greater pressure from the pump diaphragm 174. Therefore, the pressure delivered by the pump diaphragm 174 into the conduit 64 and the patient mask 18 will always exceed the pressure of the gas in the conduit 20. The ratio between the pressure in the conduit 20 and the conduit 64 is proportional to the ratio between the area of the diaphragms 174 and 162.

In another embodiment (not shown) the diaphragm motor 157 is replaced by an electric motor, such as a stepper motor, controlled by a control system to provide more accurate delivery of the substance 52.

Figure 6:
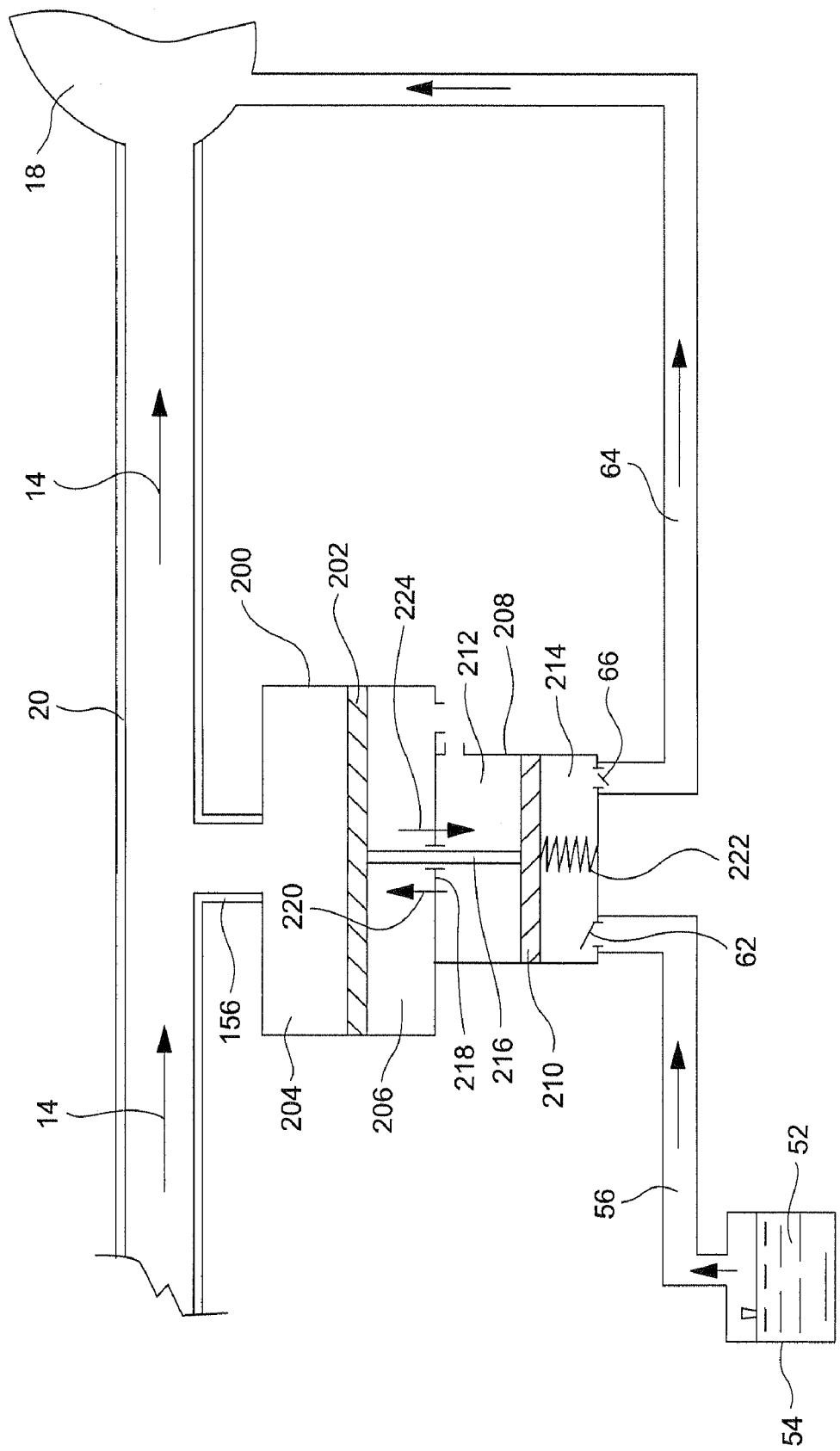
FIG. 6 is a partial schematic diagram of a substance delivery apparatus according to a fourth embodiment of the invention.

A fourth embodiment of the present invention is shown in FIG. 6, in which like reference numerals are again used to indicate like features. This embodiment is for use in conjunction with a bi-level CPAP flow generator (not shown) that delivers breathable gas at a relatively high treatment pressure to the mask during patient inhalation and at a relatively low treatment pressure during exhalation. The applicant markets such a bi-level system under the trade mark VPAP.

This embodiment includes a motor cylinder 200 having a slidable piston 202 which defines cavities 204 and 206. A pump cylinder 208 is also provided having a slidable piston 210 which defines cavities 212 and 214. The pistons 202 and 210 are connected by a connecting rod 216 which passes through an air sealed bearing 218.

The cavity 204 is connected to the conduit 20 by the branch conduit 156. The cavities 206 and 212 are open to atmosphere. The cavity 214 is connected to the source 54 of the substance 52 by the conduit 56 via the one-way valve 62. The cavity 214 is also connected to the mask 18 by the conduit 64 and the one-way valve 66.

The pistons are biased in the direction of arrow 220 by a spring 222.

The operation of the apparatus shown in FIG. 6 will now be described. During exhalation, relatively low pressure gas is passing through conduit 20 which generates only a small amount of force on the piston 202. The spring 222 overcomes this force and drives the pistons 202 and 210 in the direction of the arrow 220 thereby creating a vacuum in cavity 214. The vacuum draws the substance 52 past the one-way valve 62 and into the cavity 214.

During inhalation, relatively high pressure gas is passing through the conduit 20 which generates enough force on the piston 202 to overcome the spring 222 and drive the pistons 202 and 210 in the direction of arrow 224. This forces the substance 26 in the cavity 214 past the one-way valve 66 and into the mask 18 via the conduit 64.

The surface area of the piston 202 is larger than that of the piston 210 and the pressure generated by the piston 210 will therefore exceed that applied to the piston 202. Accordingly, the substance delivery pressure will always exceed the pressure produced by the flow generator during the inhalation phase of the breathing cycle. The ratio between the surface areas of the pistons 202 and 210 is proportional to the ratio between the breathable gas pressure and the substance delivery pressure.

Figure 7A:
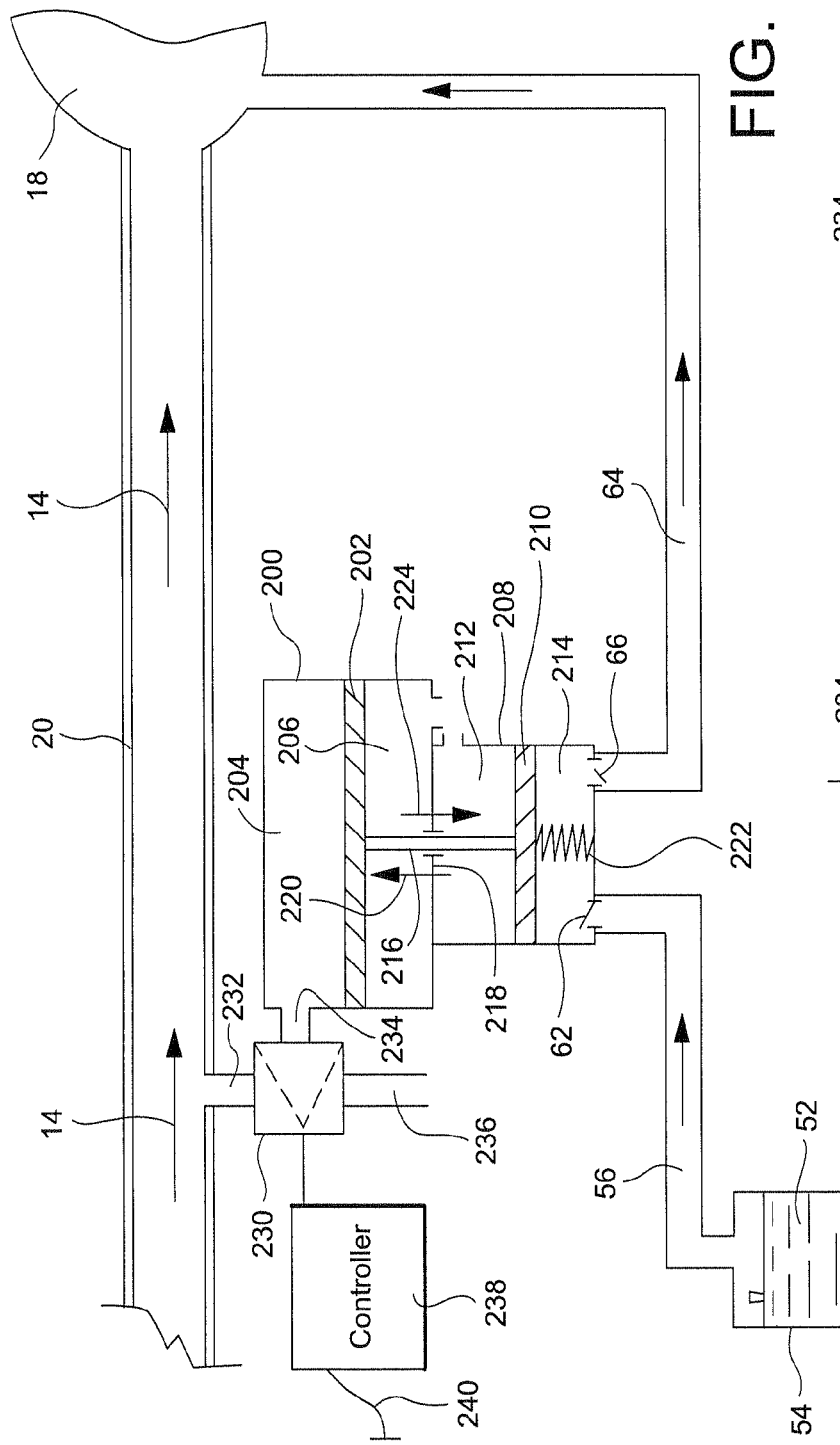
FIGS. 7a, 7b and 7c are partial schematic diagrams of a substance delivery apparatus according to a fifth embodiment of the invention.
Figure 7C:
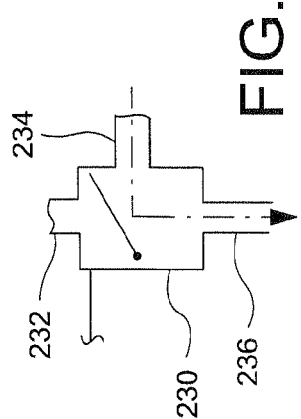
Figure 7B:
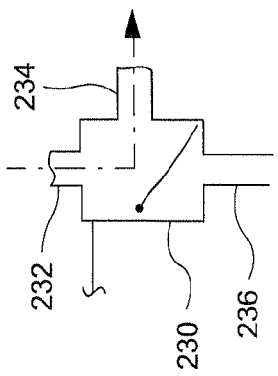

A fifth embodiment of the present invention is shown in FIGS. 7a, 7b and 7c. The fifth embodiment is essentially a modification of the fourth embodiment so it will work with a constant pressure flow generator.

The fifth embodiment includes a control valve 230 interposed between the conduit 20 and the motor cylinder 200. The valve 230 includes an inlet 232 connected to the conduit 20, a first outlet 234 connected to the cavity 204 and a second outlet 236 open to atmosphere.

The valve 230 is controlled by an electronic valve controller 238 which receives a signal 240 indicative of inhalation or exhalation, as discussed with respect to earlier embodiments.

When the signal 240 indicates inhalation, the controller 238 causes the valve 230 to move to the position indicated in FIG. 7b. In this position, the air 14 is diverted into the cavity 204 causing the pistons to move in the direction of the arrow 224 and the substance 52 to be pumped into the mask 18, as previously described.

When the signal 240 indicates exhalation, the controller 238 causes the valve 230 to move to the position shown in FIG. 7c. In this position, the air in the cavity 204 is vented to atmosphere as the pistons move in the direction of the arrow 220 under the influence of the spring 222. As previously described, this movement also causes the substance 52 to be drawn into the cavity 214.

The present invention, at least in preferred forms, provides a measured substance dose to a human or animal during inspiration only, thereby greatly reducing drug wastage.

The preferred apparatus also allows the substance to be delivered to the patient without interrupting CPAP, or similar treatment, or sleep, thereby increasing patient comfort and convenience.

The preferred apparatus also obviates the need for a patient to remember to take medicine.

The invention has been described with reference to specific examples. However, it will be appreciated by those skilled in the art that the invention may be embodied in many other forms.

The invention claimed is:

1. A substance delivery apparatus for supplying a substance to a human or animal, the substance delivery apparatus comprising:
    means for generating a flow of pressurized breathable gas;
    means for measuring the pressure of the flow of pressurized breathable gas; and
    means for delivering the substance with the flow of pressurized breathable gas to the human or animal only during inhalation, the substance being added to the flow of pressurized breathable gas at a pressure that exceeds the measured pressure of the flow of pressurized breathable gas by a predetermined pressure difference.

2. An apparatus as claimed in claim 1, further comprising means for detecting inhalation by the human or animal.

3. An apparatus as claimed in claim 2, wherein the means for detecting inhalation comprises an airflow sensor adapted to measure a volumetric flow rate of the flow of pressurized breathable gas passing through a flexible conduit in fluid communication with the means for generating the flow of pressurized breathable gas and a mask adapted to be worn by the human or animal and being adapted to generate a first input signal indicative of the breathable gas flow rate.

4. An apparatus as claimed in claim 3, further comprising a differentiating filter to derive the first signal into a second input signal indicative of acceleration or deceleration of the breathable gas to thereby indicate inhalation or exhalation respectively.

5. An apparatus as claimed in claim 1, wherein the substance is a medicinal substance in the form of a gas, mist, aerated suspension, jet, spray, or a gas mixture.

6. An apparatus as claimed in claim 1, wherein the means for delivering the substance is adapted to deliver the substance to a respiratory system of the human or animal.

7. An apparatus as claimed in claim 6, wherein the means for delivering the substance is adapted to deliver the substance to nasal airways of the human or animal.

8. An apparatus as claimed in claim 1, further including means for determining a volume of the substance to be delivered to the means for delivering the substance to the human or animal.

9. An apparatus as claimed in claim 1, wherein the means for measuring the pressure is a pressure transducer adapted to be connected to a conduit in fluid communication with the means for generating a flow of pressurized breathable gas and a patient interface adapted to be worn by the human or animal.

10. An apparatus as claimed in claim 1, wherein the means for delivering a substance is a positive displacement pump.

11. An apparatus as claimed in claim 10, wherein the positive displacement pump is a diaphragm pump.

12. An apparatus as claimed in claim 11, wherein the diaphragm pump is in fluid communication with a substance reservoir via a one-way valve adapted to allow the substance to only pass from the reservoir to the diaphragm pump.

13. An apparatus as claimed in claim 11, wherein the diaphragm pump is displaced by a linear drive.

14. An apparatus as claimed in claim 13, wherein the linear drive is an electromagnet.

15. An apparatus as claimed in claim 11, wherein a diaphragm of the diaphragm pump is displaced by a rotary to linear converter driven by a rotary drive.

16. An apparatus as claimed in claim 15, wherein the rotary drive is one of an electric direct current motor, an electric alternating current motor, a stepper motor or a brushless motor.

17. An apparatus as claimed in claim 1, wherein the means for delivering the substance is synchronized with the inhalation and an exhalation of the human or animal so that the means for delivering the substance operates in an inhalation phase during inhalation and operates in an exhalation phase during exhalation.

18. An apparatus as claimed in claim 17, wherein the means for delivering the substance is adapted to receive the substance from a reservoir during the exhalation phase and deliver the substance during the inhalation phase.

19. A substance delivery apparatus for supplying a substance to a human or animal, the substance delivery apparatus comprising:
    a flow generator configured to generate a flow of pressurized breathable gas;
    a pressure sensor to measure the pressure of the flow of pressurized breathable gas;
    an air flow sensor adapted to measure a volumetric flow rate of the flow of pressurized breathable gas;
    a positive displacement pump configured to add the substance to the flow of pressurized breathable gas at a pressure that exceeds the measured pressure of the flow of pressurized breathable gas by a predetermined pressure difference; and
    a control system configured to operate the positive displacement pump,
    wherein the substance is added to the flow of pressurized breathable gas only during a volumetric flow rate indicative of inhalation.

20. An apparatus as claimed in claim 19, further comprising a flexible conduit in fluid communication with the flow generator and a mask adapted to be worn by the human or animal, wherein the air flow sensor configured to measure the volumetric flow rate of the flow of pressurized breathable gas passing through the flexible conduit.

21. An apparatus as claimed in claim 20, wherein the air flow sensor is adapted to generate a first input signal indicative of the breathable gas flow rate.

22. An apparatus as claimed in claim 21, wherein the control system is configured to derive the first signal into a second input signal indicative of acceleration or deceleration of the breathable gas to thereby indicate inhalation or exhalation respectively.

23. An apparatus as claimed in claim 22, wherein the positive displacement pump is configured to operate in an exhalation phase synchronized with exhalation in which the displacement pump receives the substance from a substance reservoir and operate in an inhalation phase synchronized with inhalation in which the displacement pump add the substance to the flow of pressurized breathable gas.

24. An apparatus as claimed in claim 23, wherein the control system is configured to determine a volume of the substance to be delivered to the flow of pressurized breathable gas.

25. An apparatus as claimed in claim 24, wherein the positive displacement pump is a diaphragm pump.

26. An apparatus as claimed in claim 25, wherein the control system is configured to displace a diaphragm of the diaphragm pump by a distance corresponding to the determined volume of the substance to be added to the flow of pressurized breathable gas.

27. An apparatus as claimed in claim 26, wherein the diaphragm pump is in fluid communication with the substance reservoir via a one-way valve adapted to allow the substance to only pass from the substance reservoir to the diaphragm pump.

28. An apparatus as claimed in claim 27, wherein the diaphragm pump is displaced by a linear drive.

29. An apparatus as claimed in claim 28, wherein the linear drive is an electromagnet.

30. An apparatus as claimed in claim 29, wherein the diaphragm of the diaphragm pump is displaced by a rotary to linear converter driven by a rotary drive.

31. An apparatus as claimed in claim 30, wherein the rotary drive is one of an electric direct current motor, an electric alternating current motor, a stepper motor or a brushless motor.

32. A substance delivery apparatus for supplying a substance to a human or animal, the substance delivery apparatus comprising:
  a flow generator configured to generate a flow of pressurized breathable gas;
  a pressure sensor to measure the pressure of the flow of pressurized breathable gas;
  an air flow sensor adapted to measure a volumetric flow rate of the flow of pressurized breathable gas;
  a positive displacement pump configured to add the substance to the flow of pressurized breathable gas at a pressure that exceeds the measured pressure of the flow of pressurized breathable gas by a predetermined pressure difference; and
  a control system configured to operate the positive displacement pump in an inhalation phase and an exhalation phase so that the positive displacement pump receives the substance during exhalation and adds the substances to the flow of pressurized breathable gas during inhalation.

33. An apparatus as claimed in claim 32, wherein the air flow sensor is adapted to generate a first input signal indicative of the breathable gas flow rate.

34. An apparatus as claimed in claim 33, wherein the control system is configured to derive the first signal into a second input signal indicative of acceleration or deceleration of the breathable gas to thereby indicate inhalation or exhalation respectively.

* * * * *